US008084005B2

(12) United States Patent
Beer

(10) Patent No.: US 8,084,005 B2
(45) Date of Patent: Dec. 27, 2011

(54) MULTI-WELL SAMPLE PLATE COVER PENETRATION SYSTEM

(75) Inventor: Neil Reginald Beer, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 615 days.

(21) Appl. No.: 11/342,361

(22) Filed: Jan. 26, 2006

(65) Prior Publication Data

US 2007/0172393 A1    Jul. 26, 2007

(51) Int. Cl.
*B01L 3/00* (2006.01)
(52) U.S. Cl. ....... 422/569; 422/68.1; 422/243; 422/551; 422/553; 234/1; 234/46; 83/30; 83/167; 83/523
(58) Field of Classification Search .......................... None
See application file for complete search history.

(56) References Cited

U.S. PATENT DOCUMENTS

| | | | | |
|---|---|---|---|---|
| 4,076,441 A | * | 2/1978 | Byrnes | ............................ 409/293 |
| 5,232,430 A | * | 8/1993 | Nitsch | ............................ 493/341 |
| 5,342,581 A | | 8/1994 | Sanadi | |
| 5,516,490 A | | 5/1996 | Sanadi | |
| 5,741,463 A | | 4/1998 | Sanadi | |
| 5,789,251 A | * | 8/1998 | Astle | ................................ 436/48 |
| 6,077,378 A | * | 6/2000 | Bullard et al. | .................. 156/252 |
| 6,451,261 B1 | * | 9/2002 | Bodner et al. | .................... 422/99 |
| 6,880,443 B2 | * | 4/2005 | Gross et al. | ................. 83/698.91 |
| 6,939,516 B2 | | 9/2005 | Hall et al. | |
| 6,940,055 B2 | | 9/2005 | Kwasnoski et al. | |
| 6,969,449 B2 | | 11/2005 | Maher et al. | |
| 2003/0221965 A1 | * | 12/2003 | Seino et al. | .................... 204/603 |
| 2005/0047971 A1 | | 3/2005 | Clements et al. | |
| 2005/0048642 A1 | | 3/2005 | Bunn et al. | |
| 2005/0221274 A1 | | 10/2005 | Negulescu et al. | |
| 2005/0226786 A1 | | 10/2005 | Hager et al. | |
| 2005/0227241 A1 | | 10/2005 | Fang et al. | |
| 2005/0255473 A1 | | 11/2005 | Knezevic et al. | |
| 2005/0265902 A1 | | 12/2005 | Chen et al. | |
| 2005/0277125 A1 | | 12/2005 | Benn et al. | |
| 2006/0188404 A1 | * | 8/2006 | Gjerde | ............................. 422/99 |

OTHER PUBLICATIONS

ABgene, 2001, Molecular Biotechnology, vol. 19, p. 224.*
Application and Expression: PCR, RT-PCR and qPCR—Piercers; Thermo Scientific, p. 726.*
ABGene Catalog 2003-2004, pp. 161-164.*

* cited by examiner

*Primary Examiner* — In Suk Bullock
*Assistant Examiner* — Timothy G Kingan
(74) *Attorney, Agent, or Firm* — Eddie E. Scott

(57) ABSTRACT

An apparatus for penetrating a cover over a multi-well sample plate containing at least one individual sample well includes a cutting head, a cutter extending from the cutting head, and a robot. The cutting head is connected to the robot wherein the robot moves the cutting head and cutter so that the cutter penetrates the cover over the multi-well sample plate providing access to the individual sample well. When the cutting head is moved downward the foil is pierced by the cutter that splits, opens, and folds the foil inward toward the well. The well is then open for sample aspiration but has been protected from cross contamination.

12 Claims, 4 Drawing Sheets

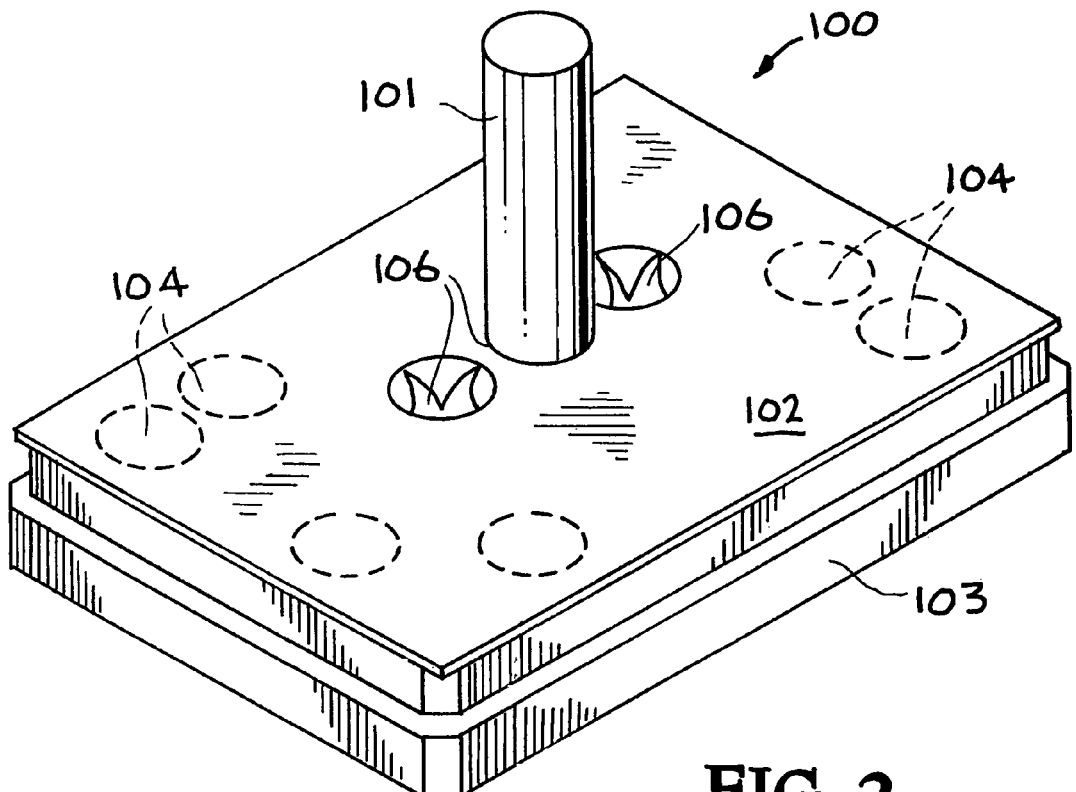
FIG. 2
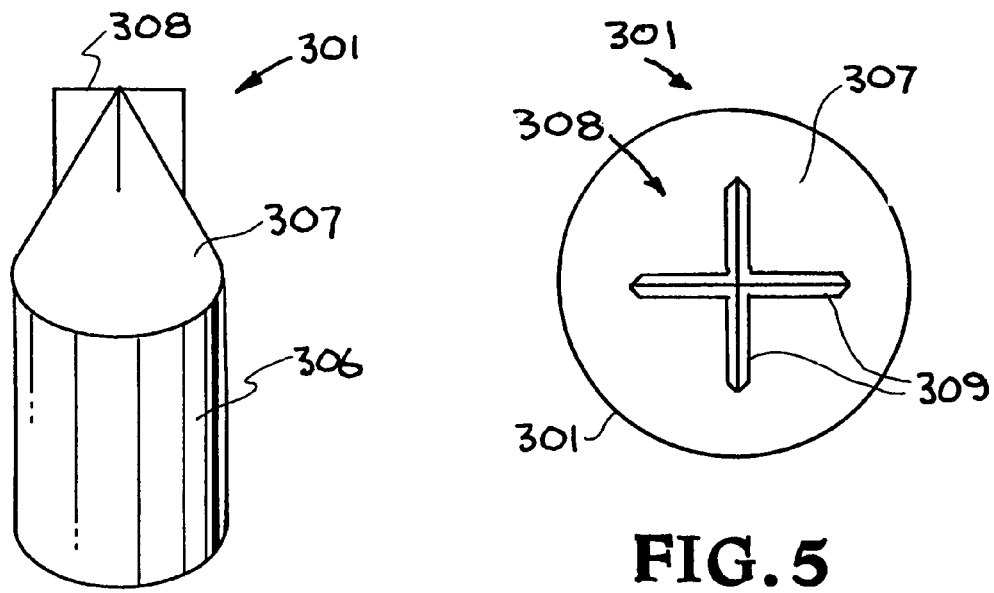
FIG. 4
FIG. 5

MULTI-WELL SAMPLE PLATE COVER PENETRATION SYSTEM

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to multi-well plates and more particularly to a multi-well sample plate cover penetration system.

2. State of Technology

United States Patent Application No. 2005/0047971 by James G. Clements et al for Multi-well Plate and Method of Manufacture published Mar. 3, 2005 provides the following state of technology information: "Assays of biochemical systems are carried out on a large scale in both industry and academia, so it is desirable to have an apparatus that allows these assays to be performed in convenient and inexpensive fashion. Because they are relatively easy to handle, are low in cost, and generally disposable after a single use, multiwell plates are often used for such studies. Multiwell plates typically are formed from a polymeric material and consist of an ordered array of individual wells. Each well includes sidewalls and a bottom so that an aliquot of sample may be placed within each well. The wells may be arranged in a matrix of mutually perpendicular rows and columns. Common sizes for multiwell plates include matrices having dimensions of 8×12 (96 wells), 16×24 (384 wells), and 32×48 (1536 wells)."

United States Patent Application No. 2005/0226786 by David Clarence Hager et al for Multi-well Apparatus published Oct. 13, 2005 provides the following state of technology information: "An optional cover may be provided for covering the open tops of the wells of the multi-well block."

U.S. Pat. No. 6,939,516 for Multi-well Plate Cover and Assembly Adapted for Mechanical Manipulation issued Sep. 6, 2005 to John P. Hall et al provides the following state of technology information: "The multi-well plates, being liquid-filled and subject to storage, have a number of lidding options available to the user. The simplest form of cover is a molded plastic lid that loosely fits over the multi-well plate. For some researchers this may provide an adequate seal, but other researchers may require a more robust cover that provides for protection from both the ingress and egress of materials into the individual wells. The nature of ingression can include the absorbence of material such as water in the presence of DMSO (dimethyl sulfoxide), a preferred storage solvent with a hygroscopic nature, and transfer of materials between wells. Egression can include the loss of volume due to evaporation or sublimation. Another form of lidding is that of an adhesive seal type cover such as Costar® Thermowell® sealers (Catalog No. 6570). An adhesive seal is approximately 3"×5" and consists of a substrate material such as a thin foil or plastic film to which an adhesive has been applied. These seals can be applied by mechanical or manual means. The adhesive seal is removed by hand as there is no mechanical device for removal. The adhesive seal provides superior sealing properties in contrast to the plastic lid but has a number of deficiencies: (1) it can only be used once; (2) its adhesive can come in contact with the stored entity; and (3) during removal if any of the stored entity is on the inner surface of the seal, it may be problematic for worker safety. Additionally, if repeated seals are applied to the same multi-well plate the adhesive tends to build up, compromising the seals of successive applications. Yet another form of lidding is the use of a heat-sealed cover such as the Abgene Easy Peel Polypropylene Sealing Film (Catalog No. AB-0745). A heat-sealed cover is 3"×5" and consists of a substrate material such as polypropylene film. Most of the multi-well plates used for storage are polypropylene. With the application of heat and pressure by means of an Abgene Combi Thermal Sealer, the heat-sealed cover can be bonded to the polypropylene multi-well plate on the plate's upper surface. This seal is in essence a molecular bond caused by the melting of the polypropylene of the respective entities. As such, the heat seal cover sets the standard for multi-well plate sealing in terms of protection from both the ingress and egress of materials into the individual wells. It can be applied by manual and mechanical means such as the Abgene 1000, a semi-automatic applicator that uses roll stock of the Abgene Easy Peel Sealing Film. However, there is no mechanical device for the removal of heat-sealed covers. Heat-sealed covers cannot be reused. Each time a heat-sealed cover is attached to the plate there can be distortion on the standoffs of the individual wells, plus polypropylene remnants, affecting the quality of future seals on the same plate."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Laboratory analysis of chemical and biological samples is a time consuming process involving hundreds to thousands of samples for a typical test. These labor driven processes have led to the development of laboratory automation systems, now commonplace, that aspirate, mix, dispense, heat, and perform other operations according to the specific experimental protocols on large numbers of samples simultaneously. Current standards include the 96-well (an 8 by 12 array) and the 384-well (a 16 by 24 array) plates that hold the liquid samples during processing and moves between robotic platforms. To keep the liquid solutions inside the well the plates are sealed, typically with an adhesive backed aluminum foil tape as the most cost effective method. (Other sealing methods are much more expensive, time consuming, and only marginally more effective, involving multi-piece assemblies with coverlocks, diaphragms, or other mechanisms. Thus they are not widely used.)

The plates are then transferred, heated, centrifuged, bead beaten (vibrated on a shaker while beads previously deposited in the wells mix the sample and breakdown fibers, cell walls, spores, and other structures), and other operations depending on the specific experiment protocol. After these processes are performed the samples then need to be aspirated for chemical detection or subsequent tests, necessitating well penetration. Cross-contamination concerns require the wells are accessed with a minimum of aerosol generation. Standard aluminum sealing tape is used in mixing and beating processes.

Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

The present invention provides an apparatus for penetrating a cover over a multi-well sample plate containing at least one individual sample well. The apparatus includes a cutting head, a cutter extending from the cutting head, and a robot. The cutting head is connected to the robot wherein the robot moves the cutting head and cutter so that the cutter penetrates the cover over the multi-well sample plate providing access to the individual sample well. When the cutting head is moved downward the foil is pierced by the cutter that splits, opens, and folds the foil inward toward the well. The well is then open for sample aspiration but has been protected from cross contamination.

The present provides an array cutting and tape folding tool that can be used for 96-well, 384-well geometries, and other geometries. The system will be robotically operating and will cut, open, and fold inward the sealing tape so that samples can be subsequently aspirated without the need for human intervention to remove the seal (an aerosol generating and contaminating process).

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 2 illustrates a system constructed in accordance with one embodiment of the present invention.

FIG. 4 shows the cutter in greater detail.

FIG. 5 is a bottom view of the cutter.

DETAILED DESCRIPTION OF THE INVENTION

Figure 1:
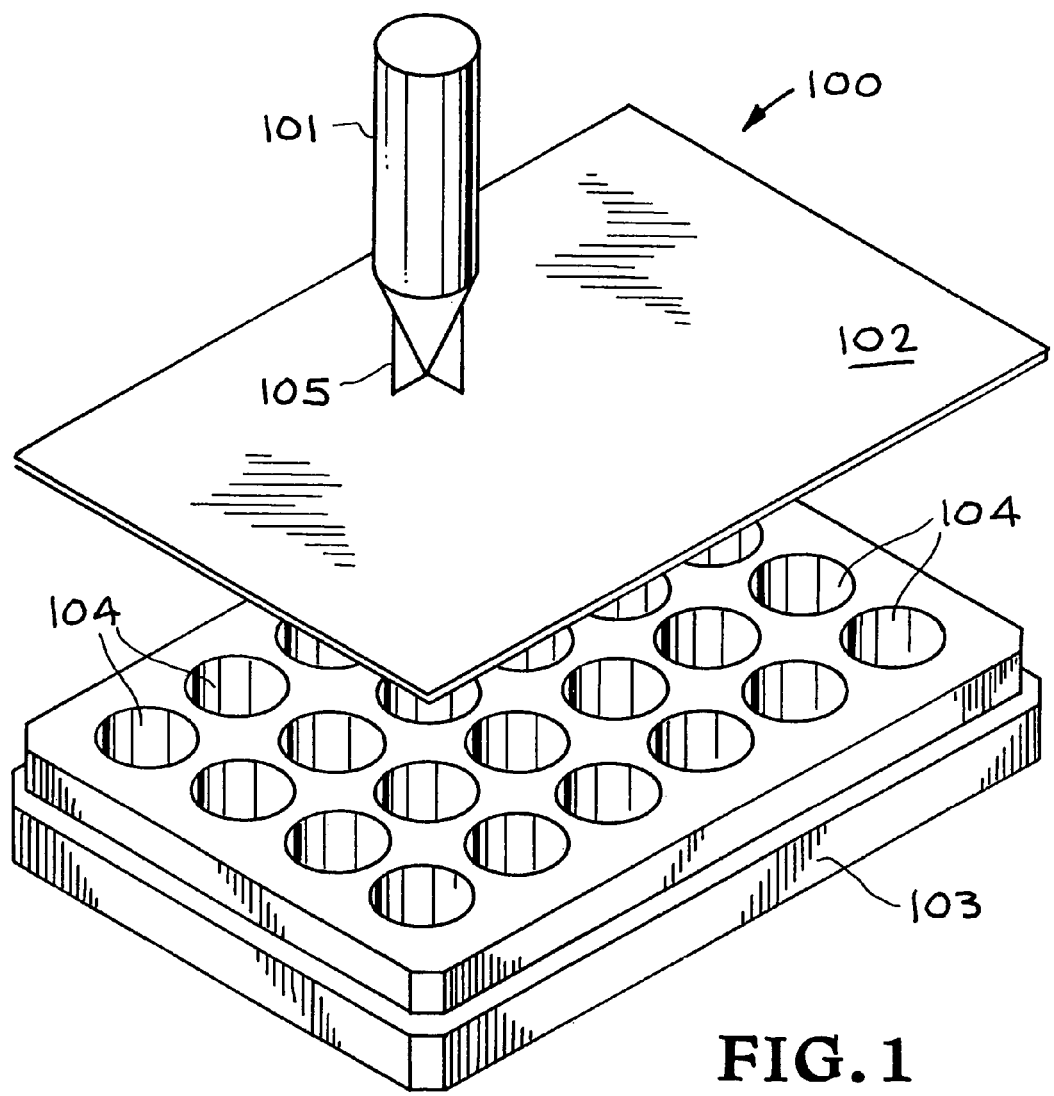
FIG. 1 is an exploded view that illustrates a system constructed in accordance with one embodiment of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIGS. 1 and 2 of the drawings, one embodiment of a multi-well sample plate cover penetration system constructed in accordance with the present invention is illustrated. This embodiment of the present invention is designated generally by the reference numeral 100. The system 100 comprises an individual well cutting head 101 positioned to penetrate a cover 102 of a multi-well sample plate 103 containing individual sample wells 104. The cutting head 101 includes a cutter 105.

Sealed wells containing liquid samples for use in biological or chemical analyses need to be penetrated for sampling and analysis. The wells are covered with a seal such as an aluminum tape or foil 102. Instead of peeling the tape 102 off the wells 104 to access the samples and potentially cross-contaminating adjacent wells with generated aerosols or adhesive strings, as was the case of the prior art, the foil 102 is pierced by the cutter 105 of the cutting head 101 that splits, opens, and folds the foil 102 inward toward the individual well 104. The wells 104 are then open for sample aspiration but have been protected from cross contamination.

The present invention not only eliminates cross contamination, it also automates other step in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Referring now to FIG. 1, an exploded view of the multi-well sample plate cover penetration system 100 is illustrated. The cover 102 is shown positioned over the multi-well sample plate 103 containing the individual sample wells 104. The multi-well sample plate 103 is used in biological or chemical analyses. The wells 104 are covered by cover 102. In the embodiment shown, the cover 102 is an aluminum tape or foil. The well cutting head 101 is shown positioned above the cover 102. When the well cutting head 101 is moved downward the foil 102 is pierced by the cutter 105 that splits, opens, and folds the foil 102 inward toward the well 104. The well 104 is then open for sample aspiration but has been protected from cross contamination.

The plate 102 includes a peripheral skirt and an upper surface having the array of wells 104 each of which is capable of receiving an aliquot of sample to be assayed. Preferably, the plate 102 conforms to industry standards for multiwell plates; that is to say, a plate bordered by a peripheral skirt, laid out with 96 wells in an 8×12 matrix (mutually perpendicular 8 and 12 well rows). In addition, the height, length, and width are preferably conform to industry standards. The present invention, however, can be implemented in any type of multiwell plate arrangement including 384 and 1536 wells, and is not limited to any specific number of wells or any specific dimensions.

The multi-well plate 102, is liquid-filled and may be subject to storage. The simplest form of cover is a molded plastic lid that loosely fits over the multi-well plate 102. For some researchers this may provide an adequate seal, but other researchers may require a more robust cover that provides for protection from both the ingress and egress of materials into the individual wells. The nature of ingression can include the absorbence of material such as water in the presence of DMSO (dimethyl sulfoxide), a preferred storage solvent with a hygroscopic nature, and transfer of materials between wells. Egression can include the loss of volume due to evaporation or sublimation. As illustrated in FIG. 1, a form of lidding is that of an adhesive seal type cover 102 such as Costar® Thermowell® sealers (Catalog No. 6570). An adhesive seal is approximately 3"×5" and consists of a substrate material such as a thin foil or plastic film to which an adhesive has been applied. These seals can be applied by mechanical or manual means.

The system 100 provides an array cutting and tape folding tool 101 that can be used for 96-well, 384-well geometries, and other geometries. In other embodiments of the present invention that will be described subsequently, the system will be robotically operating and will cut, open, and fold inward the sealing tape so that samples can be subsequently aspirated without the need for human intervention to remove the seal (an aerosol generating and contaminating process).

The present invention not only eliminates cross contamination, it also automates other step in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Referring now to FIG. 2, the multi-well sample plate 103 is shown covered by the cover 102. The plate 102 includes a peripheral skirt and an upper surface having the array of wells 104 each of which is capable of receiving an aliquot of sample to be assayed. Preferably, the plate 102 conforms to industry standards for multiwell plates; that is to say, a plate bordered by a peripheral skirt, laid out with 96 wells in an 8×12 matrix (mutually perpendicular 8 and 12 well rows). In addition, the height, length, and width preferably conform to industry standards. The present invention, however, can be implemented in any type of multiwell plate arrangement including 384 and 1536 wells, and is not limited to any specific number of wells or any specific dimensions.

The multi-well plate 102, is liquid-filled and may be subject to storage. The simplest form of cover is a molded plastic lid that loosely fits over the multi-well plate 102. For some researchers this may provide an adequate seal, but other researchers may require a more robust cover that provides for protection from both the ingress and egress of materials into the individual wells. The nature of ingression can include the absorbence of material such as water in the presence of DMSO (dimethyl sulfoxide), a preferred storage solvent with a hygroscopic nature, and transfer of materials between wells. Egression can include the loss of volume due to evaporation or sublimation. As illustrated in FIG. 2, a form of lidding is that of an adhesive seal type cover 102 such as Costar® Thermowell® sealers (Catalog No. 6570). An adhesive seal is approximately 3"×5" and consists of a substrate material such as a thin foil or plastic film to which an adhesive has been applied. These seals can be applied by mechanical or manual means.

Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

The foil 102 has been pierced by the cutter of the cutting head 101 that splits, opens, and folds the foil 102 inward toward the individual well 104 and provides an access opening 106. The wells 104 are then open for sample aspiration but have been protected from cross contamination. The cutting head 101 is moved from one well to another well and provides openings 106 for access to the wells. Rinsing of the cutting head 101 is performed if desired between cutting operations on individual wells 104.

The present invention not only eliminates cross contamination, it also automates other steps in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Figure 3:
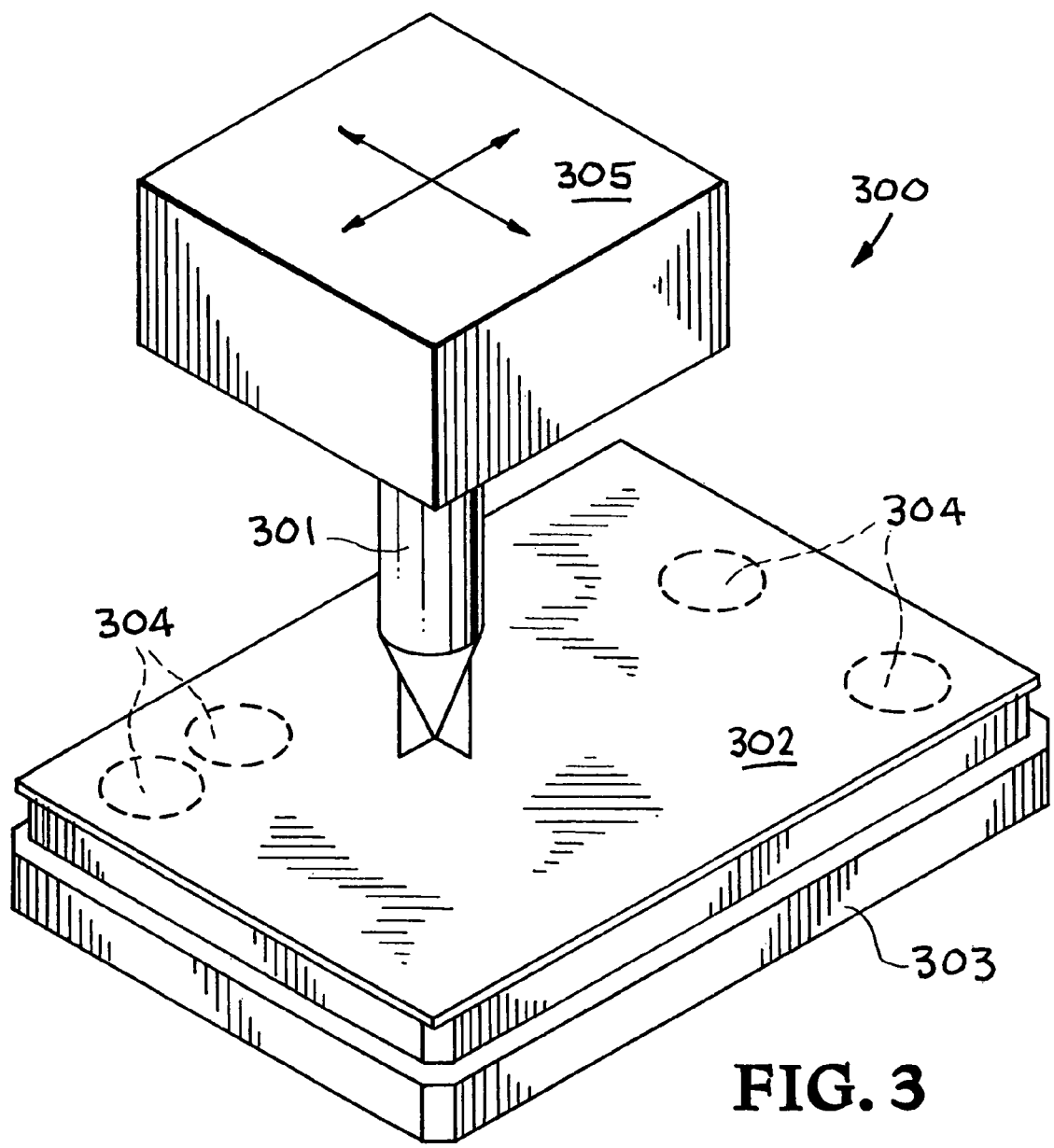
FIG. 3 illustrates as system constructed in accordance with another embodiment of the present invention.

Referring now to FIG. 3, another embodiment of a multi-well sample plate cover penetration system constructed in accordance with the present invention is illustrated. This embodiment of the present invention is designated generally by the reference numeral 300. The system 300 comprises an individual well cutting head 301 positioned to penetrate a cover 302 of a multi-well sample plate 303 containing individual sample wells 304. The cutting head 301 is driven by a robot 305.

Sealed wells containing liquid samples for use in biological or chemical analyses need to be penetrated for sampling and analysis. The wells are covered with a seal such as an aluminum tape or foil 302. Instead of peeling the tape 302 off the wells 304 to access the samples and potentially cross-contaminating adjacent wells with generated aerosols or adhesive strings, as was the case of the prior art, the foil 302 is pierced by the cutter 305 of the cutting head 301 that splits, opens, and folds the foil 302 inward toward the individual well 304. The wells 304 are then open for sample aspiration but have been protected from cross contamination.

The cutter head 301 is positioned by the robot 305 above the cover 302 in the precise position for penetrating the cover 302 above an individual well 304. The robot 305 moves the cutting head 301 downward toward the foil 302. The cutter head 301 pierces the foil 302 so that the foil 302 is split open and folded inward toward the well 304. The well 304 is then open for sample aspiration but has been protected from cross contamination.

The system 300 provides an array cutting and tape folding tool 301 that can be used for 96-well, 384-well geometries, and other geometries. In other embodiments of the resent invention that will be described subsequently, the system will be robotically operating and will cut, open, and fold inward the sealing tape so that samples can be subsequently aspirated without the need for human intervention to remove the seal (an aerosol generating and contaminating process).

The present invention not only eliminates cross contamination, it also automates other steps in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Referring now to FIG. 4, the cutting head 301 is shown in greater detail. The cutting head 301 includes a cylindrical shaft 306, a conical tip 307, and a cutting tool 308. The cutting head 301 is moved by the robot 305 shown in FIG. 3 to cause the cutting tool 308 to contact and penetrate the cover 302 over the wells of the multi-well sample plate.

The cutter tool 308 pierces the foil 302 so that the foil 302 is split open and folded inward toward the well 304. The well 304 is then open for sample aspiration but has been protected from cross contamination. The present invention not only eliminates cross contamination, it also automates other steps in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Referring now to FIG. 5, a bottom view of the cutting head 301 is shown. The cutting head 301 is moved by the robot 305 shown in FIG. 3 to cause the cutting tool 308 to contact and penetrate the cover 302 over the wells of the multi-well sample plate. The cutting tool 308 portion of the cutting head 301 is in the form of an X." The cutting head 308 includes cross-shaped cutting blades. 309. The cross-shaped cutting blades 309 and the conical tip 307 cause the foil 302 to be folded inward toward the well.

In operation, the cutting head 301 is moved by the robot to cause the cutting tool 308 to contact and penetrate the cover over the wells of the multi-well sample plate. The cross-shaped cutting blades 309 form an "X" cut in the cover. The conical tip 307 moves into the "X" and cause the foil of the cover to be folded inward toward the well. The cutter tool 308 pierces the foil 302 so that the well is open for sample aspiration. The cross-shaped cutting blades 309 and the conical tip 307 cause the foil 302 to be folded inward toward the well. The well is open for sample aspiration but has been protected from cross contamination.

Figure 6:
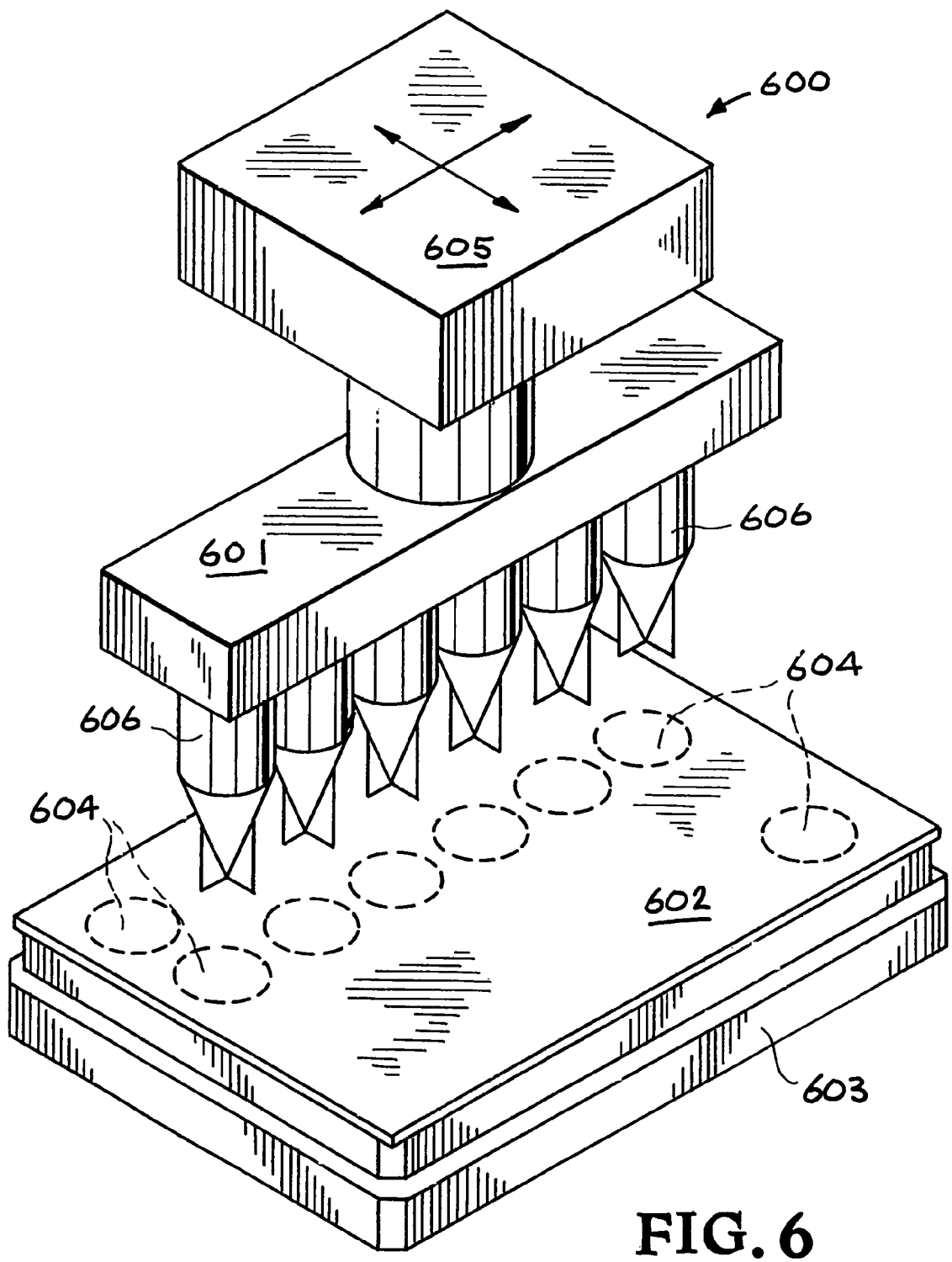
FIG. 6 illustrates another system constructed in accordance with one embodiment of the present invention.

Referring now to FIG. 6, yet another embodiment of a multi-well sample plate cover penetration system constructed in accordance with the present invention is illustrated. This embodiment of the present invention is designated generally by the reference numeral 600. The system 600 comprises an array of well cutting heads 601 positioned to penetrate a cover 602 of a multi-well sample plate 603 containing a multiplicity of individual sample wells 604. The array of cutting heads 601 is driven by a robot 605. The array of cutting heads 601 includes a multiplicity of individual cutting heads 606. The individual cutting heads 606 are positioned in one or more rows along the array of well cutting heads 601. The row or rows are spaced at the same intervals as the individual sample wells 604 in the multi-well sample plate 603. This assures that an individual cutting head 606 will be immediately above a corresponding ample well 604.

The wells 606 contain liquid samples for use in biological or chemical analyses. The wells 606 are covered with a seal such as an aluminum tape or foil 602. The wells 606 need to be penetrated for sampling and analysis.

The array of cutter heads 601 is moved and positioned by the robot 605. The array of cutter heads 601 is moved so that the individual cutting heads 606 are above the cover 602 in the precise position for penetrating the cover 602 above a corresponding multiplicity of individual wells 604. The robot 605 moves the array of cutting heads 601 and the individual cutting heads 606 downward toward the foil 602. The individual cutting heads 606 pierce the foil 602. Each individual split is made so that the foil 602 is split open and folded inward toward the individual well 604. The well 604 is then open for sample aspiration but has been protected from cross contamination.

Instead of peeling the tape 602 off the wells 604 to access the samples and potentially cross-contaminating adjacent wells with generated aerosols or adhesive strings, as was the case of the prior art, the foil 602 is pierced by the cutter 605 of the cutting head 601 that splits, opens, and folds the foil 602 inward toward the individual well 604. The wells 604 are then open for sample aspiration but have been protected from cross contamination.

The system 600 provides an array of cutting and tape folding tools 606 that can be used for 96-well, 384-well geometries, and other geometries. In other embodiments of the resent invention that will be described subsequently, the system will be robotically operating and will cut, open, and fold inward the sealing tape so that samples can be subsequently aspirated without the need for human intervention to remove the seal (an aerosol generating and contaminating process).

The present invention not only eliminates cross contamination, it also automates other steps in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

Referring again to FIG. 6, the system 600 provides an array cutting and tape folding tool 401 that can be used for 96-well, 384-well geometries, and other plate geometries. In other embodiments of the present invention that will be described subsequently, the system will be robotically or manually operating and will cut, open, and fold inward the sealing tape on all the wells on the plate simultaneously so that samples can be subsequently aspirated without the need for human intervention to remove the seal (an aerosol generating and contaminating process). Rinsing of the cutting heads 606 is performed by the robot 605 at its rinse station if desired between cutting operations on the entire plate. In this specific embodiment, all 96, 384, or other well plates can be prepared for aspiration by just one motion of the array cutting and folding tool 606. This tool 606 can be either hand operated, or designed with a robotic interface as another embodiment. Because this array cutting and tape folding tool 401 cuts and penetrates all wells on an individual plate simultaneously, it will require specific embodiments depending on the geometry of the plate to be accessed in addition to specific embodiments to operate on just one column of wells at a time verses the entire plate.

The present invention not only eliminates cross contamination, it also automates other steps in the experimental protocol. Current standard accepted laboratory protocols are so concerned with the proven cross contamination vector of the tape removal process (the tape is currently peeled back from the entire plate by hand generating adhesive strings that cross wells and jostling the then open wells) that much slower and more time consuming processes are performed instead of tape sealing such as removal of the samples from the plate and processing with individual capillary tubes, a tremendous disadvantage in both time and expense.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for analyzing a sample contained in an individual sample well of a sample plate having at least one individual sample well, wherein there is a cover over the sample plate and the individual sample well, the apparatus adapted for penetrating the cover over the sample plate and the individual sample well containing the sample in the at least one individual sample well, comprising:

a cutting head adapted to be positioned over the sample plate and over the cover over the sample plate wherein said cutting head includes a cylindrical shaft having a central axis, a cutting tool extending from said cylindrical shaft having a central axis, said cutting tool having a cutting blade, said cutting blade comprising a multiplicity of cutting sections and a conical tip, wherein said multiplicity of cutting sections are attached to said conical tip and extend horizontally with respect to said central axis of said cylindrical shaft and provide a shape for splitting the cover open over the individual sample well, folding the cover inward over the individual sample well, and adapted to be positioned over the sample plate, over the cover over the sample plate, and over the individual sample well, and a robot connected to said cutting head and said cutting tool, said robot acting to move said cutting head and cutting tool to a position wherein said cutting tool is positioned over the sample plate, over the cover over the sample plate, and over the individual sample well, said robot acting to move said cutting tool so that said cutting blade penetrates the cover over the sample plate folding the cover inward over the individual sample well, and providing access to the individual sample well and the sample contained in the individual sample well.

2. The apparatus of claim 1 wherein said cutting tool has a cutting blade with a multiplicity of cutting sections wherein said multiplicity of cutting sections provide crossed cutting sections providing a shape that folds the cover inward over the individual sample well.

3. The apparatus of claim 1 wherein said cutting tool has a cutting blade with a multiplicity of cutting sections wherein said multiplicity of cutting sections provide crossed cutting sections in the form of an "X" providing a shape that folds the cover inward over the individual sample well.

4. An apparatus for analyzing samples contained in a multiplicity of individual sample wells of a multi-well sample plate, wherein there is a cover over the multi-well sample plate and the multiplicity of individual sample wells, the apparatus adapted for penetrating the cover over the multi-well sample plate and at least some of the multiplicity of individual sample wells containing the samples in the multiplicity of individual sample wells, comprising:

a cutting head array adapted to be positioned over the multi-well sample plate, over the multiplicity of individual sample wells, and over the cover over the multi-well sample plate and the multiplicity of individual sample wells wherein said cutting head array includes a multiplicity of cylindrical shafts each of which has a central axis, a multiplicity of individual cutting tools extending from said cutting head array, wherein each of said multiplicity of cutting tools has a cutting blade with a multiplicity of cutting sections and a conical tip, wherein said multiplicity of cutting sections are attached to said conical tip and extend horizontally with respect to said axis of said cylindrical shaft and provide a shape for splitting the cover open over the multiplicity of sample wells, folding the cover inward over the multiplicity of sample wells, and adapted to be positioned over the multi-well sample plate, over the cover over the multi-well sample plate, and over at least some of the multiplicity of individual sample wells, and a robot connected to said cutting head array and said multiplicity of individual cutting tools, said robot acting to move said cutting head array and said multiplicity of individual cutting tools so that said multiplicity of individual cutting tools having a cutting blade penetrate the cover over the multi-well sample plate and at least some of the multiplicity of individual sample wells folding the cover inward over the multiplicity of sample wells, and providing access to at least some of the individual sample wells and the samples contained in the individual sample wells.

5. The apparatus of claim 4 wherein said cutting tools extending from said cutting head array, said multiplicity of cutting tools having a cutting blade, said cutting blade having a shape for splitting the cover open over the multiplicity of sample wells, folding the cover inward over the multiplicity of sample wells, and adapted to be positioned over the multi-well sample plate, over the cover over the multi-well sample plate, and over at least some of the multiplicity of individual sample wells are arranged in at least one row on said cutting head array.

6. The apparatus of claim 4 wherein each of said individual cutting tools has a cutting blade with a multiplicity of cutting sections wherein said multiplicity of cutting sections provide crossed cutting sections providing a shape that folds the cover inward over the individual sample well.

7. The apparatus of claim 4 wherein each of said individual cutting tools has a cutting blade with a multiplicity of cutting sections wherein said multiplicity of cutting sections provide crossed cutting sections in the form of an "X" providing a shape that folds the cover inward over the individual sample well.

8. An apparatus for analyzing a chemical or biological sample contained in an individual sample well of a sample plate having at least one individual sample well, wherein there is a foil cover over the sample plate and the individual sample well, the apparatus adapted for penetrating the foil cover over the sample plate and the individual sample well containing the chemical or biological sample in the at least one individual sample well, comprising:

a cutting head adapted to be positioned over the sample plate and over the foil cover over the sample plate wherein said cutting head includes a cylindrical shaft having a central axis, a cutting tool extending from said cylindrical shaft having a central axis, said cutting tool having a cutting blade, said cutting blade comprising a multiplicity of cutting sections and a conical tip, wherein said multiplicity of cutting sections are attached to said conical tip and extend horizontally with respect to said central axis of said cylindrical shaft and provide a shape for splitting the cover open over the individual sample well, folding the cover inward over the individual sample well, and adapted to be positioned over the sample plate, over the cover over the sample plate, and over the individual sample well, and a robot connected to said cutting head and said cutting tool, said robot acting to move said cutting head and cutting tool to a position wherein said cutting tool is positioned over the sample plate, over the foil cover over the sample plate, and over the individual sample well, said robot acting to move said cutting tool so that said cutting tool penetrates the foil cover over the sample plate folding the foil inward over the individual sample well, and providing access to the individual sample well and the chemical or biological sample contained in the individual sample well.

9. The apparatus of claim 8 wherein said cutting tool has a cutting blade with a multiplicity of cutting sections wherein said multiplicity of cutting sections provide crossed cutting sections providing a shape that folds the foil inward over the individual sample well, and providing access to the individual sample well and the chemical or biological sample contained in the individual sample well.

10. The apparatus of claim 8 wherein said cutting tool has a cutting blade with a multiplicity of cutting sections wherein said multiplicity of cutting sections provide crossed cutting sections in the form of an X providing a shape that folds the foil inward over the individual sample well, and providing access to the individual sample well and the chemical or biological sample contained in the individual sample well.

11. The apparatus of claim 8 wherein said cutter head includes a cylindrical shaft and a cutting tool extending from said cylindrical shaft, wherein said cutting tool has a cutting blade with a multiplicity of cutting sections wherein said multiplicity of cutting sections provide crossed cutting sections providing a shape that folds the foil inward over the individual sample well, and providing access to the individual sample well and the chemical or biological sample contained in the individual sample well.

12. A method of analyzing a sample contained in an individual sample well of a sample plate having at least one individual sample well, wherein there is a cover over the sample plate and the individual sample well, the apparatus adapted for penetrating the cover over the sample plate and the individual sample well containing the sample in the at least one individual sample well, comprising the steps of:
  providing a cutting head wherein said cutting head includes a cylindrical shaft having a central axis;
  providing a cutting tool extending from said cylindrical shaft having a central axis;
  providing a cutting blade extending from said cutting tool, said cutting blade comprising a multiplicity of cutting sections and a conical tip, wherein said multiplicity of cutting sections are attached to said conical tip and extend horizontally with respect to said central axis of said cylindrical shaft;
  providing a robot connected to said cutting head, said cutting tool, and said cutting blade;
  using said robot for positioning said cutting head, said cutting tool, and said cutting blade over the sample plate and over the cover over the sample plate;
  using said robot for moving said cutting head, said cutting tool, and said cutting blade to a position wherein said cutting tool is positioned over the sample plate, over the cover over the sample plate, and over the individual sample well; and
  using said robot for moving said cutting head, said cutting tool, and said cutting blade so that said cutting blade penetrates the cover over the sample plate folding the cover inward over the individual sample well, and providing access to the individual sample well and the sample contained in the individual sample well.

* * * * *